( 12 ) United States Patent
Valen

(10) Patent No.: US 7,547,210 B1
(45) Date of Patent: Jun. 16, 2009

(54) UNIVERSAL, MULTIFUNCTIONAL, SINGLE UNIT, ROTARY OSTEOTOME

(75) Inventor: Maurice Valen, Holliswood, NY (US)

(73) Assignee: Impladent, Ltd, Holliswood, NY (US)

( * ) Notice: Subject to any disclaimer, the term of this patent is extended or adjusted under 35 U.S.C. 154(b) by 985 days.

(21) Appl. No.: 10/668,805

(22) Filed: Sep. 24, 2003

(51) Int. Cl.
*A61C 3/02* (2006.01)
*A61C 5/00* (2006.01)

(52) U.S. Cl. ........................................ 433/165; 433/215

(58) Field of Classification Search ................. 433/165, 433/173–174, 215; 606/80, 180
See application file for complete search history.

(56) References Cited

U.S. PATENT DOCUMENTS 5,139,098 A * 8/1992 Blake .......................... 175/269
5,261,818 A * 11/1993 Shaw .......................... 433/165
6,325,627 B1 * 12/2001 Ashman ....................... 433/173
6,364,662 B1 * 4/2002 Kumar ......................... 433/165

* cited by examiner

*Primary Examiner*—John J Wilson
*Assistant Examiner*—Heidi M Eide
(74) *Attorney, Agent, or Firm*—Maxine Barasch & Associates, PLLC

(57) ABSTRACT

A multifunctional surgical rotary instrument with a corrosion resistant wear reducing hard coating, to be used in a surgical dental motor driven handpiece for preparing an osteotomy for implant insertion, combining the functions of six surgical instruments is described. The multifunctional surgical rotary instrument has structural features that provide the functions of a crestal bone height reducer, an osteotomy locator, an osteotomy lateral redirector, osteotomy drill, tapered countersink, and an osteocompressor. These structural features include a dual-lobed single plane tip that remains where the drilling is initiated without wandering, and facilitates the precise location of the osseous implant site. Advantageously, the instrument can save time and cost in the implant procedure.

1 Claim, 2 Drawing Sheets

UNIVERSAL, MULTIFUNCTIONAL, SINGLE UNIT, ROTARY OSTEOTOME

FIELD OF THE INVENTION

The present invention generally relates to surgical rotary instruments to be used with a surgical dental motor for manipulating bone, and specifically relates to tool bits, including drilling bits, cutting bits, cutting tips of osteotomes, counterbores, manual osteotomes, and the like, for particular use in the field of oral surgery and, more particularly, in the field of dental implantology.

BACKGROUND OF THE INVENTION

Dental implants are surgically implanted in a patient's jawbone to provide anchors for prosthetic devices such as artificial teeth, crowns, bridges, dentures, and the like. Dental implants allow people who lose their teeth to be able to comfortably smile, speak, and chew.

Typically, the first step for installing an implant involves making an incision in the patient's gum or gingiva. Next, a hole or implant osteotomy is formed in the jawbone of the patient, which may involve widening pre-existing cavities, forming fresh osteotomies, or splitting the ridge and filling the voids with a synthetic bone material. The implant is then fixtured into the osteotomy.

The step of forming an osteotomy typically involves seven to ten drilling procedures of a prerequisite implant geometry to form a hole in the patient's jawbone, utilizing Xrays, CT-scan, and vital monitoring instrumentation. It may take half an hour to simply remove and reinstall drill bits in the surgical motor. This can be a difficult and time-consuming procedure and can cause discomfort and trauma for the patient, partially due to the pain, edema, and shock involved with the penetration of a relatively large drilling bit into the patient's jawbone. Bone necrosis, which may accompany the use of hand instrumentation (i.e., rongeurs, etc.), is also possible. Drilling in high bone densities can further exacerbate and complicate the osteotomy preparation.

The high rotational drilling speeds typically involved in the procedure can generate a significant amount of heat. High frictional forces and torques between the bone and the drilling bit can also result. Large amounts of heat can cause bone necrosis, and the high torque increases the risk of bone fracture and breakage of the drilling bit. Again, this adds to the trauma and suffering of the patient, and can inhibit the desired healing of the bone and osseointegration of the implant (Roberts W E, Turley P K, Brezniak N, et al., Bone Physiology and Metabolism, *Calif Dent Assoc J.*, 1987:15:54-61; Brunski, J B, Biomechanial Factors Affecting the Bone-Dental Implant Interface, *Clinical Materials,* 1992:10:153-201).

In some cases, large dental counterbores are utilized to countersink the osteotomy for receiving a particularly configured large dental implant. Counterbores involve removal of bone material and can result in restricting vascularity and bone loss (Valen M and Locante W M, LaminOss Immediate-Load Implants: Part I-Introducing Osteocompression in Dentistry, *J Oral Implantol,* 26(3):177-184, 2000) or all of the abovementioned disadvantages.

Conventionally, a handheld osteotome is used to form an osteotomy in soft bone. Typically, an osteotome has a larger tip and is manually manipulated by the dental practitioner in an artful, uncontrolled osteocompressive fashion to dilate the soft, bony material. Again, using rotary drill bits and twist drills can result in some or all of the abovementioned disadvantages. Physically, drill bits and twist drills can laterally wander at the time of drilling at the intended osteotomy site, possibly resulting in damage to surrounding nerves, teeth, and/or other vital anatomical sites.

Often, the use of a crestal bone height reducer is required to cut uneven crestal bone to create a leveled implant osseous platform. The use of crestal bone height reducers involves removal of bone material and can cause some or all of the abovementioned disadvantages.

As indicated above, it can be difficult and time-consuming to effectively perform osteotomy preparation procedures with handheld instrumentation. It is also very important to minimize discomfort, trauma, and damage to the patient. Moreover, the drilling bits, counterbores, threadformers, and osteotome cutting tips are exposed to frictional forces and corrosive elements both in the patient's mouth and possibly during sterilization. In many cases, this results in these instruments needing frequent replacement, since wear and corrosion reduce their effectiveness.

Changing from one to another of these tools during surgery takes time from the oral surgeon, adds to the time the surgical site is open and exposed to oral bacteria, and extends the time the patient must be anesthetized. Changing from one to another of these tools also adds time to the implant procedure and cost due to equipment needed, and wear and tear on the surgical instrumentation.

Various inventions have been created to alleviate several of the aforementioned problems with the implant procedure. For example, U.S. Pat. No. 6,364,662 B1, issued to Ajay Kumar on Apr. 2, 2002 for DIAMOND-LIKE CARBON COATED DENTAL INSTRUMENT, describes a tool bit for preparing an osteotomy in the jawbone of a patient. In an effort to reduce the number of tools required to prepare an osteotomy, KUMAR's tool bit is a single tool comprising drilling and cutting bits, depth bands, and osteotomes, and is coated with a carbon coating/film. The tool bit may also be swapped out with other bits to accomplish the functions of threadformers, counterbores, and cutting tips.

The purpose of the carbon coating is to reduce the coefficient of friction between the tool bit and the jawbone, and improve the cutting performance. Some of the other benefits and advantages arise as a consequence of the coating properties of high mechanical hardness (wear resistance), corrosion resistance, and high thermal conductivity.

KUMAR's patent does not speak to an osteotomy locator or lateral osteotomy redirector, but instead has a distal tip composed of a multi-lobed, multi-planar tip. A multi-lobed, multi-planar distal tip will physically wander using a handheld instrument when function is initiated, making the precise location of the osseous implant site difficult.

SUMMARY OF THE INVENTION

In accordance with the present invention, there is provided a multifunctional surgical rotary instrument to prepare an osteotomy. The instrument has a novel design, combining features in its unique structure that provide the functions of six separate surgical instruments in one tool bit. The instrument comprises the functions of a crestal bone height reducer, an osteotomy locator, an osteotomy lateral redirector, an osteotomy drill, a tapered countersink, and an osteocompressor.

The present invention has a mounting shank for interfacing with the motor driven handpiece of an osteotomy cutting and drilling system, and a dual-lobed, single plane design distal tip, which remains where the drilling is initiated, and facilitates the precise location of the osseous implant site. The tip is redirectable, permitting the avoidance of vital features in the jawbone by the lateral movement of the redirectable tip. The cutting and drilling blade of the invention has multifaceted cutting edges, which are used to reduce crestal bone height.

It is an object of this invention to reduce the number of surgical instruments used to prepare an osteotomy for implants.

It is another object of this invention to reduce the number of operative steps required in preparing an osteotomy.

It is another object of this invention to eliminate the cost of six separate surgical instruments.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF THE PREFERRED EMBODIMENT

Figure 1:
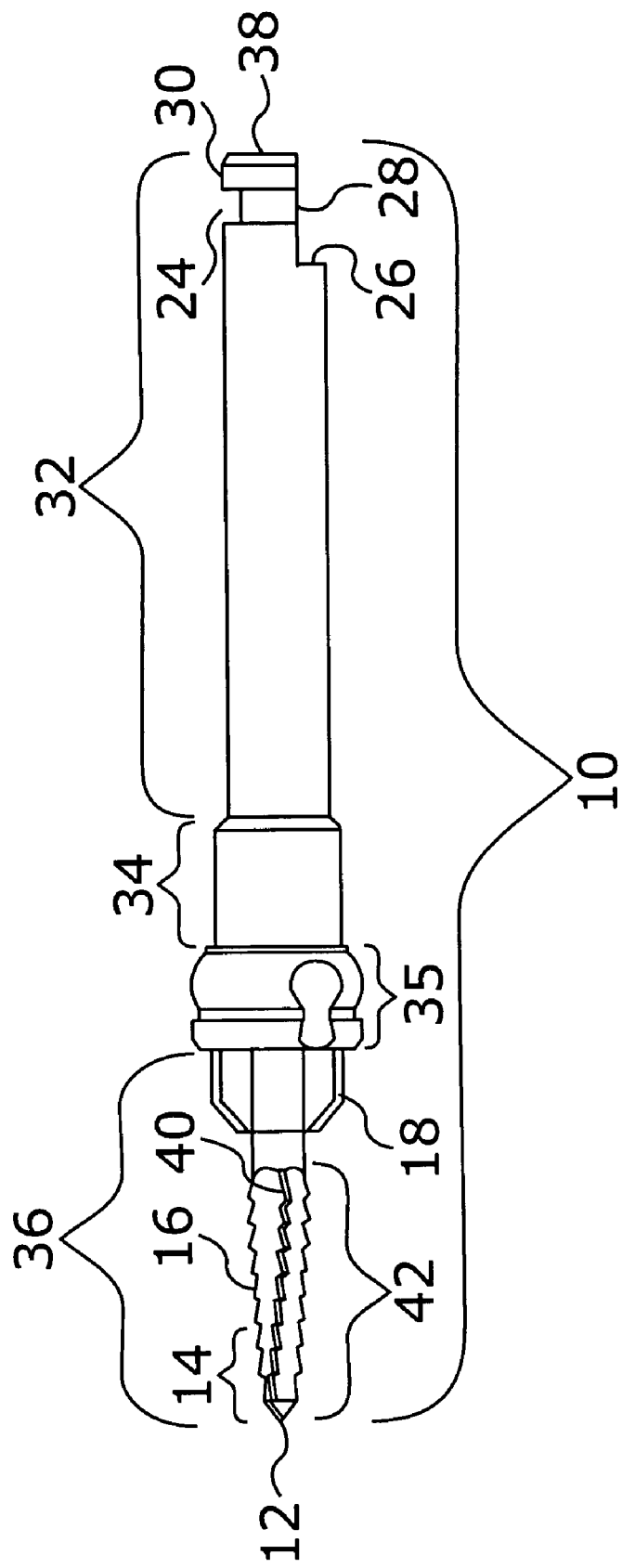
FIG. 1 is a front elevational view of the multifunctional, rotary, dental osteotome.

The invention is a multifunctional, rotary, dental osteotome for use with a dental surgical motor in dental implant preparation, wherein the instrument comprises a single tool bit incorporating the functions of what traditionally has been six individual tool bits. The functions included in the single instrument are: a crestal reducer, an osteotomy locator, an osteotomy lateral redirector, an osteotomy drill, a tapered countersink, and an osteocompressor.

The invention is particularly concerned with, and will be described primarily in connection with, dental implant surgery involving the creation of a precise osteotomy in the jawbone of a human patient. Other embodiments of the present invention will become readily apparent to those skilled in the art, from both the detailed description and reference to the attached figures. As such, the invention is not limited to any particular embodiment disclosed. Other embodiments of the present invention may be equally useful for cutting and drilling into various other human bones, possibly extending to use in connection with animal bones, and including orthopedic applications that require larger diameters than those used in the preferred embodiment.

Historically, the first step in preparing the osteotomy is to perform tissue reflection, followed by a crestal bone marking. Traditionally, a round bur mounted on a drill extension and provisional bridge is used. Crestal bone marking is done by positioning the provisional bridge intraorally. The external irrigation and drilling speed is set at approximately 1000 to 1500 rpm. Using the pre-drilled channel in the designated implant tooth of the guide-stent, the site(s) are marked on crestal bone. A pilot twist drill is then mounted on a drill extension to initiate the pilot osteotomy.

While using the positioned provisional bridge as a guided stent, the bone is penetrated to a designated depth following the desired trajectory at drilling speeds of 1000 to 1500 rpm or less. The provisional bridge is then removed and a depth spade or twist drill is used to prepare the implant osteotomy according to the appropriate depth reference line for the selected implant at drilling speeds of 1000 to 1500 rpm or less. The osteotomy is then enlarged with a finishing spade or twist drill at 1000 to 1500 rpm or less. The osteotomy depth is then verified with a depth gauge probe.

At this time, it is optional to countersink the cortical bone to 1-2 mm. After verification of the depth, the initial bone threading is performed with a bone tap at a speed of 50 rpm. The final step in preparing the osteotomy before implant insertion uses a synthetic bone grafting material inferiorly and superiorly to the implant site.

The procedure for preparing an osteotomy thus described requires many surgical instruments. A disadvantage is the possible time added to the procedure necessitated by interchanging each required drill bit. Time is a significant factor during the procedure because the patient will be anesthetized and the surgical site is open to oral bacteria. In addition, the pre-operative procedure takes longer because each drill bit being used requires proper sterilization. Every separate pre-operative step adds time and cost to the procedure. In addition to time, the cost of several surgical instruments is added to the implant procedure.

In contrast to the many surgical instruments typically required in preparing an osteotomy, the multifunctional, rotary osteotome of the present invention can, unassisted, accomplish all of the procedures previously described.

Referring now to FIG. 1, a front elevational view of the multifunctional, rotary, dental osteotome 10 is shown. The multifunctional, rotary, dental osteotome 10 generally includes a drilling and cutting portion 36 and an osteocompressive portion 35 connected to a linking member 34, which is further connected to a mounting shank 32 for attachment to the surgical motor. The drilling and cutting portion 36 of the multifunctional, rotary, dental osteotome 10 generally includes a dual lobed single plane osteotomy locator tip 12, an osteotomy lateral redirection portion 14 that transitions into a drilling/cutting and crestal bone height reducer 42, and a tapered countersink and gross crestal bone height reducer 18.

Figure 2:
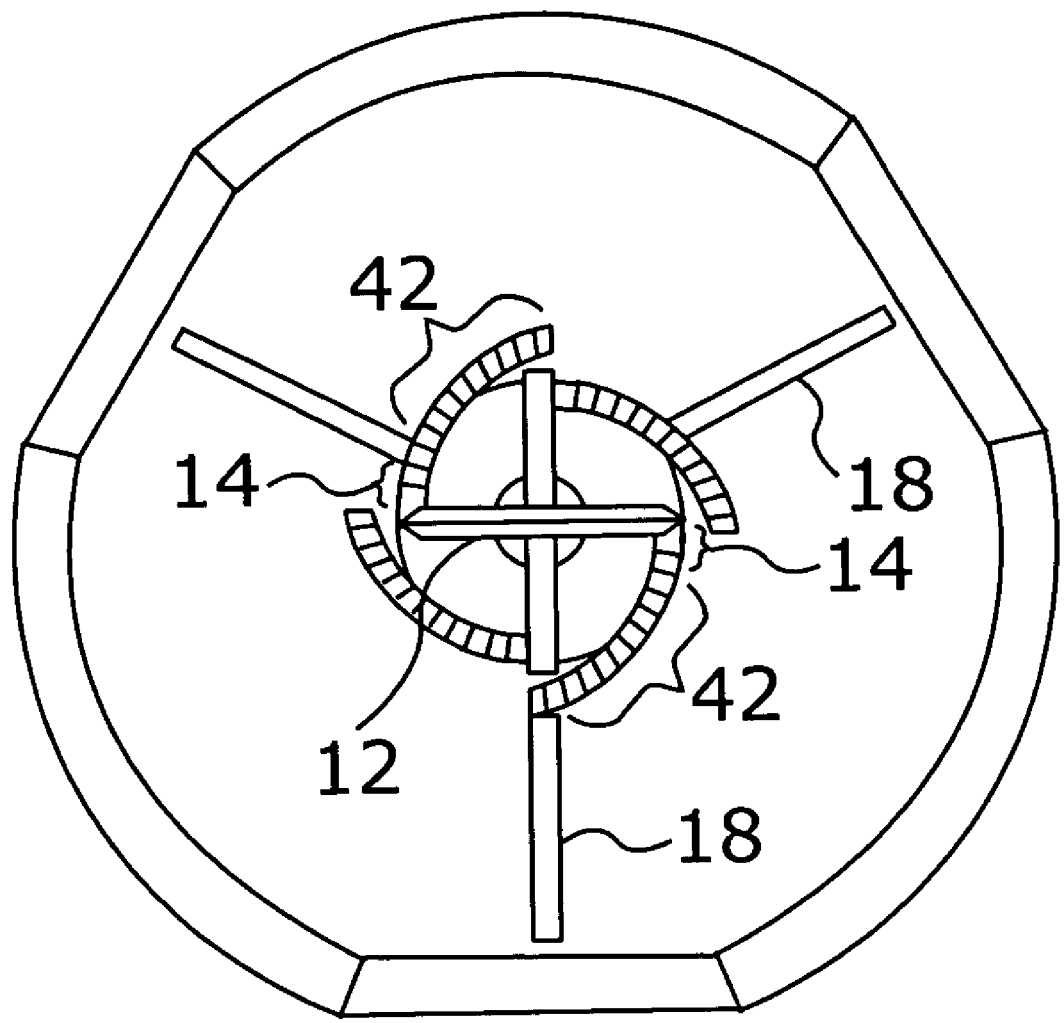
FIG. 2 is an end view of the multifunctional, rotary, dental osteotome.

Referring now to FIG. 2, an end view of the multifunctional, rotary, dental osteotome 10 is shown. The end view shows the planar nature of the osteotomy locator tip 12, and the flutes with multiple cutting edges that form the lateral redirection portion 14, and the drilling/cutting crestal bone height reducer 42 and a tapered countersink and gross crestal bone height reducer 18.

In one embodiment, at least a portion of the tool bit or dental instrument 10 is coated with a coating or film 16 for purposes of reducing friction between the bone and the cutting surface and hardening the surgical instrument for longer efficiency and less wear and tear. A variety of coating materials may be used to achieve the desired result. The coating material 16 can comprise, for example, diamond-like carbon (DLC) coating, a ceramic coating, a tungsten carbide coating, a titanium nitride coating, an aluminum titanium nitride coating, tungsten disulfide coating, or other similar material such as diamond dust particulates or a combination thereof. The general use and structure of these coating materials is well known in the art.

One advantage of the coating material 16 is that it provides a reduced coefficient of friction (enhanced lubrication) between the jawbone and the coated dental instrument of the present invention and improves the cutting performance. Some of the other benefits and advantages arise as a consequence of the coating material 16 properties of high mechanical hardness (wear resistance), corrosion resistance, and high thermal conductivity. Some or all of these desirable properties of the coating material 16 translate into reduced discomfort for the patient; reduced chances of accidents, bone fracture, and bone necrosis; increased operational ease for the dental surgeon, saving valuable time; and reduction in the cost of the implant procedure.

In one embodiment, the tool bit 10 is a drilling bit for forming an implant-receiving osteotomy in the patient's jawbone. The drilling bit 10 generally comprises a mounting shank 32 for attachment to the surgical motor, a cutting head 36 and an osteocompression head 35, joined by a linking member 34. The mounting shank 32 is generally cylindrical in shape and includes a proximal end or chuck 38, which is sized and configured to be received in handpieces of conventional dental drilling systems. The chuck 38 includes a generally I-shaped flat side 28, which defines a step 26 and a generally semicircular disk 30 above and adjacent to a generally semicircular groove 24. Such a configuration for the chuck 38 is typically employed in the dental industry for connecting or interfacing dental tool bits to dental drills or handpieces.

The linking member 34 is generally cylindrical in shape and mechanically connects the mounting shank 32 and the drilling and cutting head 36. In one embodiment, the linking member 34 is also coated with a coating material 16. The coating materials 16 can reduce adhesion of any bone chips or other debris to the linking member 34, making it easier to clean and sterilize the drilling bit 10. The coating material 16 also improves the corrosion resistance of the linking member 34.

In one embodiment, the cutting head 36 generally includes a plurality of flutes with a plurality of multifaceted side cutting edges 40. The side cutting edges 40 terminate transitioning into a tip or osteotomy locator 12, of the cutting head 36. In another embodiment, the cutting head 36 includes four side cutting edges 40. In another embodiment, the entire cutting head 36 is coated with a coating material 16 from one of the group of materials, for example, diamond-like carbon (DLC) coating, a ceramic coating, a tungsten carbide coating, a titanium nitride coating, an aluminum titanium nitride coating, tungsten disulfide coating, or other similar material such as diamond dust particulates or a combination thereof.

In one embodiment, the drilling bit 10 has a length of about 31.0 mm (1.220 inches). In another embodiment, the mounting shank 32 has a length of about 16.5 mm (0.65 inches), the cutting head 36 has a length of about 11.5 mm (0.45 inches), the distal end of the cutting head comprises the redirectable tip and has a length of about 2.0 mm (0.08 inches), the osteocompressive head 35 has a length of about 2.0 mm (0.08 inches), and the linking member 34 has a length of about 3.0 mm (0.12 inches). In other embodiments, the drilling bit 10 may be dimensioned and configured in a wide variety of manners, as required or desired, depending on the particular nature of the osteotomy to be formed.

In one embodiment, the cutting head 36 is dimensioned and configured to provide a cutting or osteotomy diameter of about 1.2 mm to 1.7 mm (0.05 to 0.06 inches). In another embodiment, the cutting head 36 is dimensioned and configured to provide a cutting or osteotomy diameter in the range from about 1.5 mm (0.06 inches) to about 6.0 mm (0.24 inches). In another embodiment, the cutting head 36 is dimensioned to form an osteotomy having sufficient depth to house configured dental implants with lengths ranging from approximately 8 mm (0.31 inches) to 18 mm (0.71 inches). In other preferred embodiments, the cutting head 36 may be dimensioned and configured in a wide variety of manners, as required or desired, depending on the particular nature of the osteotomy to be formed and the implant to be used.

Preferably, the drilling bit 10 is fabricated from stainless steel, and more preferably from UNS S45500 (ASTM-A564). In one embodiment, the drilling bit 10 is heat treated, electropolished and passivated prior to the application of the coating 16. In other embodiments, the drilling bit 10 may be fabricated from a wide variety of materials, such as other metals, alloys, ceramics, or plastics as required or desired, giving due consideration to the goal of providing reduced friction and improved drilling efficiency.

The drilling bit 10 is preferably manufactured by machining and/or grinding operations. In other embodiments, the drilling bit 10 may be manufactured by casting, forging and/or molding, among other known manufacturing technologies.

It is desirable to clean the surface of the tool bit 10 prior to applying the coating material 16. This facilitates better adherence of the coating material 16 to the passivated surface of the tool bit 10. Preferably, this cleaning process utilizes ultrasonic cleaning followed by a plasma cleaning of the tool bit 10. The plasma cleaning step includes bombardment of the tool bit 10 by suitable ions, such as argon ions. The cleaning process and application of the coating can be performed by any one of a number of commercial coating providers.

Preferably, at least a portion of the drilling bit 10 is coated with a coating material 16, one of the group of materials including, for example, diamond-like carbon (DLC) coating, a ceramic coating, a tungsten carbide coating, a titanium nitride coating, an aluminum titanium nitride coating, tungsten disulfide coating, or other similar materials such as diamond dust particulates or a combination thereof. In one embodiment, the cutting head 36, the osteocompressive head 35, and the linking member 34 are coated with the coating material 16. In another embodiment, only the cutting head 36 is coated with the coating material 16.

It is preferred that the mounting shank 32 not be coated with the coating diamond-like carbon (DLC) to maintain good frictional grip and reduce the creation of unwanted carbon particulate matter when the mounting shank 32 is engaged with the handpiece or drill. In alternative embodiments, some or all of the mounting shank 32 may be coated with the coating material 16, as required or desired. In one embodiment, the chuck 38 of the mounting shank 32 is coated with the coating material 16. Advantageously, the reduced friction provided by the coating material 16 on the chuck 38 facilitates in the insertion/removal of the drilling bit 10 into/from the handpiece.

In general, a coating or film material, such as one of the group of materials including, for example, diamond-like carbon (DLC) coating, a ceramic coating, a tungsten carbide coating, a titanium nitride coating, an aluminum titanium nitride coating, tungsten disulfide coating, or other similar material such as diamond dust particulates or a combination thereof, may be applied to selected surfaces of the tool bit 10 in a wide variety of configurations, as required or desired, giving due consideration to the goal of reducing friction and improving performance. The thickness of the coating material 16 may be selected as required or desired, giving due consideration to the goals of providing reduced friction and improved drilling and cutting efficiency and designated function.

In one embodiment, the coating material 16 has a coefficient of friction of approximately 0.1. In another embodiment, the coating material 16 has a coefficient of friction in the range from approximately 0.01 to 0.1. In other embodiments, the coating material 16 can have a lower or higher coefficient of friction as needed or desired, giving due consideration to the goal of achieving one or more of the advantages of the present invention.

In one embodiment, the cutting head 36 generally comprises an osteotomy locator 12, an osteotomy lateral redirection portion 14 comprising the first part of element 42, a drilling/cutting and crestal bone height reducer 42, and a tapered countersink/counterbore and gross crestal bone height reducer 18. The redirection portion 14, which is the first part of element 42, comprises the first 2 mm of the element, and the redirectable portion may be moved laterally to avoid vital features in the jawbone.

The general use and structure of dental counterbores are known in the art. The general construction of the counterbore includes cutting/counterboring edges or flutes. The crestal bone height reducer 42 is used to create a leveled implant osseous platform by moving the reducer in a buccal-lingual nonlinear motion that may be circular, oval, or another nonlinear motion to avoid creating striations in the leveled osseous platform by linear motion of the multifaceted cutting edges of the cutting and drilling blade 36 against the bone. The crestal bone height reducer 42 and/or the tapered countersink and gross crestal bone height reducer 18 may be used as bone particulate harvesters. Bone particulates thus harvested may be mixed with synthetic bone grafting material around implants to modify and fill in bony structures.

In another, the cutting head 36 generally comprises an osteotomy locator 12, an osteotomy lateral redirection portion 14, a drilling/cutting and crestal bone height reducer 42 having a twisted/spiral geometry of flutes for bone removal, a tapered countersink/counterbore and gross crestal bone height reducer 18, and an osteocompressor 35.

A method for drilling and cutting to prepare an osteotomy in a jawbone, comprising the steps of:
  a) using a cutting and drilling blade with a osteotomy locator tip of a multifunctional dental surgical tool to precisely locate an osseous implant site and prevent wandering and slipping of said tip to perform crestal bone marking;
  b) using a redirectable tip of said cutting and drilling blade to avoid bone and tissue anatomical vital sites in a patient's jawbone;
  c) using a crestal bone height reducer operatively formed from said cutting and drilling blade, to create a leveled implant osseous platform by moving said cutting and drilling blade in a buccal-lingual, nonlinear motion;
  d) using said crestal bone height reducer to harvest bony particulate material;
  e) using a tapered countersink of said multifunctional dental surgical tool to create a counterbore in cortical bone of said jawbone;
  f) using a gross osseous crestal bone height reducer of said multifunctional dental surgical tool to harvest bony particulate materials;
  g) using an osteocompressor operatively connected to said gross osseous crestal bone height reducer to compress the osseous site, completing the preparation of said osteotomy in said jawbone; and
  h) using a synthetic bone graft material mixed with said bony particulate material to reconstruct bone structures.

Since other modifications and changes varied to fit particular operating requirements and environments will be apparent to those skilled in the art, the invention is not considered limited to the examples chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A method for drilling and cutting to prepare an osteotomy in a jawbone, comprising the steps of:
  a) using a cutting and drilling blade with a dual lobed single plane osteotomy locator tip of a single, one-piece multifunctional dental surgical tool to precisely locate an osseous implant site and prevent wandering and slipping of said tip to perform crestal bone marking;
  b) using a redirectable tip of said cutting and drilling blade to avoid bone and tissue anatomical vital sites in a patient's jawbone;
  c) using a crestal bone height reducer operatively formed as serrated edges on said cutting and drilling blade, to create a leveled implant osseous platform by moving said cutting and drilling blade in a buccal-lingual, nonlinear motion;
  d) using said crestal bone height reducer to harvest bony particulate material;
  e) using a tapered countersink of said single, one-piece multifunctional dental surgical tool to create a counterbore in cortical bone of said jawbone; wherein the tapered countersink further defines a gross osseous crestal bone height reducer to harvest bony particulate material;
  f) using an osteocompressor operatively connected to said gross osseous crestal bone height reducer to compress the osseous site, completing the preparation of said osteotomy in said jawbone; and
  g) using a synthetic bone graft material mixed with said bony particulate material to reconstruct bone structures.

\* \* \* \* \*